(12) United States Patent
Holdsworth et al.

(10) Patent No.: US 9,731,261 B2
(45) Date of Patent: Aug. 15, 2017

(54) PROCESS COMPRISING TWO REACTION ZONES AND APPARATUS THEREFORE

(71) Applicant: Johnson Matthey Davy Technologies Limited, London (GB)

(72) Inventors: Duncan David Holdsworth, London (GB); Julian Stuart Gray, London (GB)

(73) Assignee: Johnson Matthey Davy Technologies Limited, London (GB)

( * ) Notice: Subject to any disclaimer, the term of this patent is extended or adjusted under 35 U.S.C. 154(b) by 0 days.

(21) Appl. No.: 15/116,089

(22) PCT Filed: Jan. 15, 2015

(86) PCT No.: PCT/GB2015/050005
§ 371 (c)(1),
(2) Date: Aug. 2, 2016

(87) PCT Pub. No.: WO2015/121611
PCT Pub. Date: Aug. 20, 2015

(65) Prior Publication Data
US 2017/0173548 A1     Jun. 22, 2017

(30) Foreign Application Priority Data
Feb. 17, 2014     (GB) .................................. 1402782.5

(51) Int. Cl.
| | |
|---|---|
| *C07C 45/38* | (2006.01) |
| *B01J 8/00* | (2006.01) |
| *B01J 8/04* | (2006.01) |
| *B01J 8/06* | (2006.01) |

(52) U.S. Cl.
CPC ........... *B01J 8/0449* (2013.01); *B01J 8/0492* (2013.01); *B01J 8/065* (2013.01); *C07C 45/38* (2013.01); *B01J 2208/024* (2013.01)

(58) Field of Classification Search
CPC ........ C07C 45/38; B01J 8/0449; B01J 8/0492
USPC .......................................................... 568/487
See application file for complete search history.

(56) References Cited

U.S. PATENT DOCUMENTS

| | | |
|---|---|---|
| 2,462,413 A | 2/1949 | Meath |
| 3,959,383 A | 5/1976 | Northeimer |
| 4,450,301 A | 5/1984 | McMillan et al. |
| 2005/0016830 A1 | 1/2005 | Kaibel et al. |
| 2011/0017348 A1 | 1/2011 | Tanimoto et al. |

FOREIGN PATENT DOCUMENTS

| | | |
|---|---|---|
| WO | 9312032 A1 | 6/1993 |
| WO | 2006091005 A1 | 8/2006 |
| WO | 2012146904 A1 | 11/2012 |

OTHER PUBLICATIONS

International Search report for PCT/GB2015/050005 mailed Aug. 10, 2015, 10 pages.

*Primary Examiner* — Sikarl Witherspoon
(74) *Attorney, Agent, or Firm* — Armstrong Teasdale LLP

(57) ABSTRACT

In a process for carrying out a chemical reaction gaseous reactants are supplied to a first reaction zone including a first catalyst having a first particle equivalent diameter. The first reaction zone is operated such that when the reactants are contacted with the first catalyst a portion of the reactants is converted to the desired product. An intermediate stream of unreacted reactants and the desired product is removed and passed to a second reaction zone including a tubular reactor. Tubes of the reactor are catalyst carriers containing a second catalyst having a second particle equivalent diameter smaller than the first particle equivalent diameter. The second reaction zone is operated such that when the unreacted reactants are contacted with the second catalyst, at least some of the unreacted reactants are converted to the desired product. A product stream is then recovered. Apparatus for carrying out the process is also described.

20 Claims, 4 Drawing Sheets

Detail A

PROCESS COMPRISING TWO REACTION ZONES AND APPARATUS THEREFORE

The present invention relates to a process for carrying out a chemical reaction. More particularly, it relates to a process for carrying out a partial oxidation reaction. Still more particularly, it relates to a process for the production of formaldehyde by oxidation of methanol or precursors of methanol such as methylal. In a second aspect it relates to a reactor for carrying out the process.

Formaldehyde is conventionally produced by the vapour phase partial oxidation of methanol, at near atmospheric pressure, in the presence of a catalyst. There are two commercially accepted methods. In one method, a silver catalyst is used. In this method the methanol, nitrogen and oxygen are passed over a shallow bed of the catalyst.

The second method uses a metal oxide catalyst, typically a mixture of iron and molybdenum oxides, which are contained within the tubes of a tubular reactor. The mixture of methanol, nitrogen and oxygen flow down through the tubes and come into contact with the catalyst where reaction occurs.

The oxidation reaction of methanol is highly exothermic and the reaction heat is therefore removed by means of a cooling medium which is circulated, or else evaporated, on the outside of the tubes.

Two primary reactions take place within the reactor tube. The first is the desired partial oxidation of methanol to formaldehyde and the second is the undesirable further oxidation or combustion of the produced formaldehyde to carbon monoxide and possibly even to carbon dioxide. It will be understood that other reactions such as the formation of di-methyl-ether from methanol, formation of methyl formate and the like may occur. However this application is directed to the primary reactions detailed above.

A typical formaldehyde reactor operates at high methanol conversion, with conversions of 99% or more being achieved. However the yield of formaldehyde removed from the reactor is generally less than 93%. This is because the conditions within the reactor used to achieve high methanol conversions to formaldehyde also lend themselves to the undesired conversion of formaldehyde to carbon oxides, the formation of which lowers the overall yield to the desired formaldehyde.

The main contributors to the operating costs of producing formaldehyde are the consumption of methanol and the consumption of electricity. The impact of these costs can, to an extent, be offset if as much of the methanol fed to the reactor is converted to desired product as possible. The amount of electricity required is related to the pressure drop through the catalyst bed. This is because a higher pressure drop through the bed means that a higher inlet pressure is required and thus there is a higher electricity consumption requirement for the compressor or blower that is supplying the mixture of nitrogen/oxygen and methanol to the reactor. Thus, to minimise the electricity element of the operating cost, the pressure drop through the catalyst bed down the tube has to be minimised. This is achieved by using larger catalyst particle sizes. Since catalyst particles may be a range of shapes, their relative size can be expressed in terms of the catalyst particle equivalent diameter. This defines the size in terms of the diameter of a sphere that has the equivalent characteristics as the catalyst particle. The catalyst particle equivalent diameter can be expressed as 6×(volume of catalyst/surface area of particle).

Typically the catalyst shapes used in the formaldehyde process have a catalyst particle equivalent diameter in the range of 1 to 6 mm. These shapes may be simple spheres. Alternatively, more complex shapes may be used as these not only minimise pressure drop but also maximise surface area.

However, whilst this catalyst particle equivalent diameter of catalyst can assist in minimising pressure drop, the range means that the thickness of the particle presents a limitation to the mass transfer processes associated with the desired and undesired reactions. For the desired reaction, it is necessary for the methanol and oxygen molecules to diffuse through the bulk of the catalyst particle until the reactant molecules reach an active catalyst site where the reaction to formaldehyde proceeds. Thus the gas molecules have to travel down a pore in the catalyst.

Once the formaldehyde molecule has been formed inside a pore in the catalyst particle, it must then diffuse out of the catalyst particle into the bulk gas flowing over the catalyst bed. Problems arise if during the diffusion out of the catalyst, the formaldehyde molecule reaches an active catalyst site as there is the possibility for the undesired reaction to carbon oxides to take place if oxygen atoms are also present.

Whilst reduction in catalyst particle equivalent diameter would minimise the risk of the produced formaldehyde encountering a further active site within the catalyst particle, any reduction in catalyst particle equivalent diameter would result in an unacceptable increase in pressure drop.

A compromise therefore has to be made between the yield of formaldehyde that can be achieved and the pressure drop through the bed. This compromise dictates the catalyst particle size that is commonly found in industrial plants.

Further, if a finely divided catalyst were used in a bid to reduce the reaction to carbon oxides, in addition to leading to the problem associated with the pressure drop, it would also lead to an increased rate of reaction which in turn would lead to an increase in peak bed temperature as it is difficult to remove the heat from the catalyst in the centre of the tube. This is problematic since any significant increase in the catalyst bed temperature results in a significant reduction in catalyst life due to the volatility of some of the molybdenum compounds in the catalyst.

One approach that has been considered to improve the process is to vary the catalyst composition axially down the reactor tube. In U.S. Pat. No. 6,518,463 a process and fixed bed reactor for oxidizing methanol in a reactant gas feed stream to formaldehyde is described. The process comprises introducing the reactant gas feed stream into an upstream region containing a first metal molybdate catalyst which is substantially free of a volatile $Mo/MoO_3$ species under oxidizing conditions to form a partially oxidized reactant gas feed stream. This partially oxidized stream is then introduced under oxidizing conditions into a downstream region containing a second metal molybdate catalyst to further oxidize any residual methanol contained therein. Thus in the first stage of the process where the hottest temperatures are present, the catalyst contains less volatile molybdenum species which would otherwise sublime at the operating conditions thereby reducing the catalyst lifetime as the resulting molybdenum deposits further down the tube and increases the pressure drop. Whilst this arrangement may offer some advantages, a conversion of only 85% or more and a selectivity of only 90% or more are noted.

An alternative approach is discussed in U.S. Pat. No. 8,513,470. In this process, a fixed bed is used for the oxidation of methanol to formaldehyde. The bed comprises at least two layers having different catalytic activity, the layer of lower activity is comprised in the part of the bed from which the reactant gas mixture enters and its activity is calibrated so that the maximum hot spot temperature in the layer is between 350° C. and 430° C. and is higher than the maximum hot spot temperature of the layer of greater activity formed by pure catalyst. During the period in which the situation of the maximum hot spot temperature of the layer of lower activity remains at the above values, the conversion of methanol is suggested to be higher than 96 mol %.

Whilst these suggestions offer some advantages, they are directed to maximising the life of the catalyst. They do not address the low yields associated with the ongoing reaction of the desired formaldehyde to carbon monoxide and/or carbon dioxide.

It is therefore desirable to find a process that maximises the conversion of methanol to formaldehyde whilst maximising the yield of formaldehyde by minimising the conversion of formaldehyde to carbon monoxide. Further, it is desirable to do this whilst maintaining a pressure drop that is comparable to conventional reactors to avoid increased electricity costs and whilst maintaining a temperature profile that does not lead to deterioration in catalyst life such as that caused by increased losses of molybdenum where that is used as the catalyst.

It has been noted by the present inventors, that in the conventional tubular reactors for forming formaldehyde using an iron molybdenum catalyst, the formation rate of carbon monoxide only becomes significant once the standing concentration of formaldehyde in the gas flowing through the reactor exceeds a minimum level. In particular, it has been found that up to 50% of the methanol can be converted to formaldehyde before any significant loss of formaldehyde to carbon monoxide takes place. However, as the reactor gas flows down the reactor tube, more and more carbon monoxide is produced as the methanol concentration reduces to the target exit concentration.

Similar problems are noted with other reactions such as partial oxidation reactions where compound A is reacted to compound B in the presence of a catalyst and, if compound B is not removed from the active sites on the catalyst, compound B can be further oxidised to compound C or even to complete oxidation products such as carbon dioxide and water. The problems are particularly exacerbated where the catalyst used is of the unsupported type and the reaction process has mass transfer limitations due to the catalyst pore size and the size and shape of the compounds diffusing into and out of the pores.

It has now been found that some or all of the problems detailed above can be addressed by carrying out a first portion of the conversion in a conventional tubular reactor packed with catalyst having a conventional catalyst particle equivalent diameter, i.e. of the order of about 1 mm to about 6 mm, and then completing the conversion in a second reaction zone configured to enable a smaller catalyst particle equivalent diameter to be utilised by allowing the resulting heat of reaction to be removed efficiently so that the temperature profile can be controlled.

WO 2011/048361, the contents of which are incorporated herein by reference, describes a carrier for particulate catalysts. The catalyst carrier comprises:
an annular container for holding catalyst in use, said container having a perforated inner wall defining a tube, a perforated outer wall, a top surface closing the annular container and a bottom surface closing the annular container;
a surface closing the bottom of said tube formed by the inner wall of the annular container;
a skirt extending upwardly from the perforated outer wall of the annular container from a position at or near the bottom surface of said container to a position below the location of a seal;
and a seal located at or near the top surface and extending from the container by a distance which extends beyond an outer surface of the skirt.

These catalyst carriers enable the heat generated in the reaction to be efficiently removed from the catalyst. Thus these catalyst carriers can be used in the second reaction zone to enable the smaller particle equivalent diameter catalyst to be used.

Thus according to the present invention there is provided a process for carrying out a chemical reaction comprising:
supplying gaseous reactants to a first reaction zone comprising a first catalyst of a first catalyst particle equivalent diameter;
operating said first reaction zone such that when the reactants are contacted with the first catalyst a portion of the reactants are converted to the desired product;
removing an intermediate stream comprising the unreacted reactants and the desired product and passing the stream to a second reaction zone comprising a tubular reactor wherein said tubes comprise a plurality of catalyst carriers containing a catalyst having a second catalyst particle equivalent diameter which is smaller than the first catalyst particle equivalent diameter of the first catalyst;
operating said second reaction zone such that when the unreacted reactants in the stream from the first reaction zone are contacted with the second catalyst, at least some of the unreacted reactants are converted to the desired product; and
recovering a product stream.

In one arrangement the second reaction zone will act as a polishing reactor.

The first reaction zone may be of any suitable configuration. The arrangement used will generally depend on the reaction to be carried out. Examples of suitable configurations include tubular fixed bed reactor, an adiabatic catalyst bed and fluidised bed. However the first reaction zone will not comprise the plurality of catalyst carriers which are used in the second reaction zone.

In one arrangement, the chemical reaction is one where the yield of product is restricted by the desired product undergoing a further reaction. In this arrangement, the first reaction zone will be sized such that the packed catalyst bed terminates before the effect of the further reaction becomes significant.

The chemical reaction may be a partial oxidation process. In a particularly preferred arrangement, the chemical reaction is the formation of formaldehyde from methanol or precursors thereto such as methylal. In this arrangement, the first reaction zone is generally sized such that it terminates before the carbon monoxide forming reaction becomes significant which is typically when about 50% of the methanol or methylal has been converted.

The use of the second, smaller, particle equivalent diameter catalyst in the second reaction zone minimises the opportunity for the product to undergo the further reaction which would otherwise reduce yield. The use of the catalyst carrier addresses the problem associated with pressure drop and heat transfer which would otherwise be noted with a small catalyst size.

In one arrangement, each catalyst carrier comprises:
an annular container for holding the second reaction catalyst in use, said container having a perforated inner wall defining a tube, a perforated outer wall, a top surface closing the annular container and a bottom surface closing the annular container;

a surface closing the bottom of said tube formed by the inner wall of the annular container;

a skirt extending upwardly from the perforated outer wall of the annular container from a position at or near the bottom surface of said container to a position below the location of a seal;

and a seal located at or near the top surface and extending from the container by a distance which extends beyond an outer surface of the skirt.

However, it will be understood that other configurations may be used. The configuration selected may depend on the configuration of the catalyst being used.

Where the catalyst carrier is of configuration described above in use in a vertical reactor with downflow, reactant(s) flow downwardly through the tube and thus first contacts the upper surface of the catalyst carrier. Since the seal blocks the passage of the reactant(s) around the side of the container, the top surface thereof directs them into the tube defined by the inner perforated wall of the container. The reactant(s) then enters the annular container through the perforated inner wall and then passes radially through the second catalyst bed towards the perforated outer wall. During the passage from the inner wall to the outer wall, the reactant(s) contact the second catalyst and reaction occurs. Unreacted reactant and product then flow out of the container though the perforated outer wall. The upwardly extending skirt then directs reactant and product upwardly between the inner surface of the skirt and the outer wall of the annular container until they reach the seal. They are then directed, by the underside of the seal, over the end of the skirt and flow downwardly between the outer surface of the skirt and the inner surface of the reactor tube where heat transfer takes place.

The benefits of the use of the catalyst carrier are discussed in detail in WO 2011/048361. In the context of the present invention they enable a small catalyst particle equivalent diameter to be used which will generally reduce the rate of any further reaction to the undesired component. This is made possible without incurring a significant pressure drop and providing the ability to control and preferably remove the increased reaction exotherm through the enhanced heat transfer achieved by the catalyst carrier.

For the avoidance of doubt, any discussion of orientation, for example terms such as upwardly, below, lower, and the like have, for ease of reference been discussed with regard to the orientation of the catalyst carrier as illustrated in the accompanying drawings. However, the catalyst carrier of the present invention could also be used in an alternative orientation for example horizontally. Thus the terms should be constructed accordingly.

The container will generally be sized such that it is of a smaller dimension than the internal dimension of the reactor tube into which it is to be placed in use. The seal will be sized such that it interacts with the inner wall of the reactor tube when the catalyst carrier of the present invention is in position within the tube. Parameters such as carrier length and diameter will be selected to accommodate different reactions and configurations.

Generally, a plurality of catalyst carriers will be stacked within a reactor tube. In this arrangement, the reactants/products flow downwardly between the outer surface of the skirt of a first carrier and the inner surface of the reactor tube until they contact the upper surface and seal of a second carrier and are directed downwardly into the tube of the second carrier defined by the perforated inner wall of its annular container. The flow path described above is then repeated.

The catalyst carrier may be formed of any suitable material. Such material will generally be selected to withstand the operating conditions of the reactor. Generally, the catalyst carrier will be fabricated from carbon steel, aluminum, stainless steel, other alloys or any material able to withstand the reaction conditions.

The wall of the annular container can be of any suitable thickness. Suitable thickness will be of the order of about 0.1 mm to about 1.0 mm, preferably of the order of about 0.3 mm to about 0.5 mm.

The size of the perforations in the inner and outer walls of the annular container will be selected such as to allow uniform flow of reactant(s) and product(s) through the second catalyst while maintaining the second catalyst within the container. It will therefore be understood that their size will depend on the size of the catalyst particles being used. In an alternative arrangement the perforations may be sized such that they are larger but have a filter mesh covering the perforations to ensure that the second catalyst is maintained within the annular container. This enables larger perforations to be used which will facilitate the free movement of reactants without a significant loss of pressure.

It will be understood that the perforations may be of any suitable configuration. Indeed where a wall is described as perforated all that is required is that there is means to allow the reactants and products to pass through the walls. These may be small apertures of any configuration, they may be slots, they may be formed by a wire screen or by any other means of creating a porous or permeable surface.

Although the top surface closing the annular container will generally be located at the upper edge of the or each wall of the annular container, it may be desirable to locate the top surface below the upper edge such that a portion of the upper edge of the outer wall forms a lip. Similarly, the bottom surface may be located at the lower edge of the, or each, wall of the annular container or may be desirable to locate the bottom surface such that it is above the bottom edge of the wall of the annular container such that the wall forms a lip.

The bottom surface of the annulus and the surface closing the bottom of the tube may be formed as a single unit or they may be two separate pieces connected together. The two surfaces may be coplanar but in a preferred arrangement, they are in different planes. In one arrangement, the surface closing the bottom of the tube is in a lower plane than the bottom surface of the annular container. This serves to assist in the location of one carrier on to a carrier arranged below it. It will be understood that in an alternative arrangement, the surface closing the bottom of the tube may be in a higher plane that the bottom surface of the annular container.

Whilst the bottom surface will generally be solid, it may include one or more drain holes. Where one or more drain holes are present, they may be covered by a filter mesh.

Similarly a drain hole, optionally covered with a filter mesh, may be present in the surface closing the bottom of the tube. Where the carrier is to be used in a non-vertical orientation, the drain hole, where present will be located in an alternative position i.e. one that is the lowest point in the carrier when in use.

One or more spacer means may extend downwardly from the bottom surface of the annular container. The, or each, spacer means may be formed as separate components or they may be formed by depressions in the bottom surface. Where these spacer means are present they assist in providing a clear path for the reactants and products flowing between the bottom surface of the first carrier and the top surface of a second lower carrier in use.

The spacer may be of the order of about 4 mm to about 6 mm deep. Alternatively, or additionally, spacer means may be present on the top surface.

The top surface closing the annular container may include on its upper surface means to locate the container against a catalyst carrier stacked above the container in use. The means to locate the container may be of any suitable arrangement. In one arrangement it comprises an upstanding collar having apertures or spaces therein to allow for the ingress of reactants.

The upwardly extending skirt may be smooth or it may be shaped. Any suitable shape may be used. Suitable shapes include pleats, corrugations, and the like. The pleats, corrugations and the like will generally be arranged longitudinally along the length of the carrier. The shaping of the upstanding skirt increases the surface area of the skirt and assists with the insertion of the catalyst carrier into the reaction tube since it will allow any surface roughness on the inner surface of the reactor tube or differences in tolerances in tubes to be accommodated.

Where the upwardly extending skirt is shaped, it will generally be flattened to a smooth configuration towards the point at which it is connected to the annular container to allow a gas seal to be formed with the annular container. The upstanding skirt will generally be connected to the outer wall of the annular container at or near the base thereof. Where the skirt is connected at a point above the bottom of the wall, the wall will be free of perforations in the area below the point of connection. The upstanding skirt may be flexible.

Generally, the upstanding skirt will stop at about 0.5 cm to about 1.5 cm, preferably about 1 cm, short of the top surface of the annular container.

Without wishing to be bound by any theory, it is believed that the upstanding skirt serves to gather the reactants/products from the perforated outer wall of the annular container and direct them via the shapes towards the top of the catalyst carrier collecting more reactants/products exiting from the outer wall of the annular container as they move upwardly. As described above, reactants/products are then directed down between the tube wall and the outside of the upstanding skirt. By this method the heat transfer is enhanced down the whole length of the carrier but as the heat exchange is separated from the catalyst, hotter or colder as appropriate heat exchange fluid can be used without quenching the reaction at the tube wall and at the same time ensuring that the temperature of the catalyst towards the centre of the carrier is appropriately adjusted.

The seal may be formed in any suitable manner. However, it will generally be sufficiently compressible to accommodate the smallest diameter of the reactor tube. The seal will generally be a flexible, sliding seal. In one arrangement, an O-ring may be used. A compressible split ring or a ring having a high coefficient of expansion could be used. The seal may be formed of any suitable material provided that it can withstand the reaction conditions. In one arrangement, it may be a deformable flange extending from the carrier.

The flange may be sized to be larger than the internal diameter of the tube such that as the container is inserted into the tube it is deformed to fit inside and interact with the tube.

The second reaction zone will generally comprise a plurality of tubes each containing a plurality of catalyst carriers. Coolant will then be provided around the tubes. The intermediate stream fed to the second reaction zone will therefore flow down the tubes where it will contact the second catalyst.

The first reaction zone and the second reaction zone may be located in the same or different vessels. Where they are located in separate vessels, the size and configuration of each can be optimised.

Interstage cooling may be provided between the first and second reaction zones. This may be facilitated where the first and second reaction zones are located in separate vessels.

Where the two reaction zones are located in the same vessel and where the first reaction zone is a tubular fixed bed reactor, the number and configuration of the tubes in the two zones may be the same or different. In one arrangement, the first and second zones may be contiguous, that is to say that each tube is packed with conventional catalyst in the first zone and with catalyst loaded into catalyst carriers in the second zone.

The same heat transfer fluid may be used in each reaction zone or a different heat transfer liquid may be used even when the two reaction zones are in the same vessel.

The first and second reaction zones may be operated at the same or a different temperature. The temperature(s) selected will depend on the reaction being carried out and the catalyst selected.

The first and second catalyst may be the same or different. In one arrangement, a portion of catalyst in the first and/or second reaction zone may be replaced with inerts to achieve either heating or cooling of the gas flowing down the tube. Where inerts are to be used they can be incorporated in any suitable way. In one arrangement, a portion of the tube may contain 100% inert material. This may be located at the start of the tube. No reaction will occur as the reactants flow through the area of inerts but the temperature of the gas is altered. A second way in which inerts may be included is to blend a mixture of catalyst and inerts. This can be achieved as a plurality of strata within the tube. This will assist in controlling the reaction rate and prevent excessive temperatures being developed.

The particle equivalent diameter of the first and second catalyst will depend on the catalyst and the reaction being carried out provided that the second catalyst particle equivalent diameter is smaller than the first. In one arrangement, the first catalyst particle equivalent diameter may be of the order of about 1 mm to about 6 mm. Any suitable shape of catalyst may be used. The catalyst may be spheres or may be shapes having higher surface areas. The second catalyst particle equivalent diameter may be of any size which is smaller than the first catalyst particle equivalent diameter. They will typically be of the order of about 0.1 mm and may be up to about 3 mm, where the first catalyst particle equivalent diameter is greater than 3 mm. The catalyst of the first and/or second reaction zone may be supported or unsupported.

A portion of the product stream may be recycled. This may be simply be a portion of the product stream as recovered from the second reaction zone or it may be residual gases after the desired product has been separated. The recycle may be to anywhere in the overall reaction process. However, in one arrangement, the recycle may be to one or both of the first and second reaction zones. Splitting the recycle to both zones allows more control over the tempering of the reaction in the reaction zones which can improve the yield of the desired product. The recycle may be taken directly after the second reactor or from downstream such as after some of the product has been separated.

One or more reactants may be added to the intermediate stream before it is added to the second reaction zone. In one arrangement an addition of one or more reactants will be directly to the second reaction zone.

Any suitable catalyst may be used. The catalyst selected will depend on the reaction being carried out. Where the reaction is the production of formaldehyde from methanol, the catalyst may be a silver catalyst. However, it is generally an iron/molybdenum based catalyst. Other components may also be present.

Where the process is for the production of formaldehyde, the reactor pressure will generally be from about 1.1 bar(a) to about 10 bar(a). The reactor temperature will generally be from about 250° C. to about 450° C.

Where the process of the present invention is used to produce formaldehyde from methanol, substantial benefits over conventional arrangements are achieved. For a given formaldehyde production rate, the total methanol requirement is reduced. This means that plant operating costs are reduced whilst also reducing effluent process requirements. In this connection, it will be understood that part of any unconverted methanol leaving the reactor whether from conventional processes or from the present invention have to be incinerated to ensure that the vent gas is sufficiently clean to be released into the environment. Additionally, since less oxygen is consumed in the reactor due to the lower formation of carbon monoxide, less air is required for a given formaldehyde production rate thus reducing plant size, capital cost and reducing the operating cost of the feed air blowers and any recycle gas blowers.

According to a second aspect of the present invention there is provided apparatus for carrying out a chemical reaction comprising:

means for supplying gaseous reactants to a first reaction zone comprising a first catalyst particle equivalent diameter;

means for removing an intermediate stream comprising the unreacted reactants and the desired product and passing the stream to a second reaction zone comprising a tubular reactor said wherein said tubes comprise a plurality of catalyst carriers containing a catalyst having a second catalyst particle equivalent diameter which is smaller than the first catalyst particle equivalent diameter of the first catalyst; and means for recovering a product stream.

The features of the apparatus are as discussed above in connection with the process.

The present invention will now be described, by way of example, with reference to the accompanying drawings in which.

It will be understood by those skilled in the art that the drawings are diagrammatic and that further items of equipment such as reflux drums, pumps, vacuum pumps, compressors, gas recycle compressors, temperature sensors, pressure sensors, pressure relief valves, control valves, flow controllers, level controllers, and the like may be required in a commercial plant. The provision of such ancillary items of equipment forms no part of the present invention and is in accordance with conventional chemical engineering practice.

For convenience the present invention will be described by reference to the production of formaldehyde from methanol. However, it will be equally applicable to other reactions.

Figure 1:
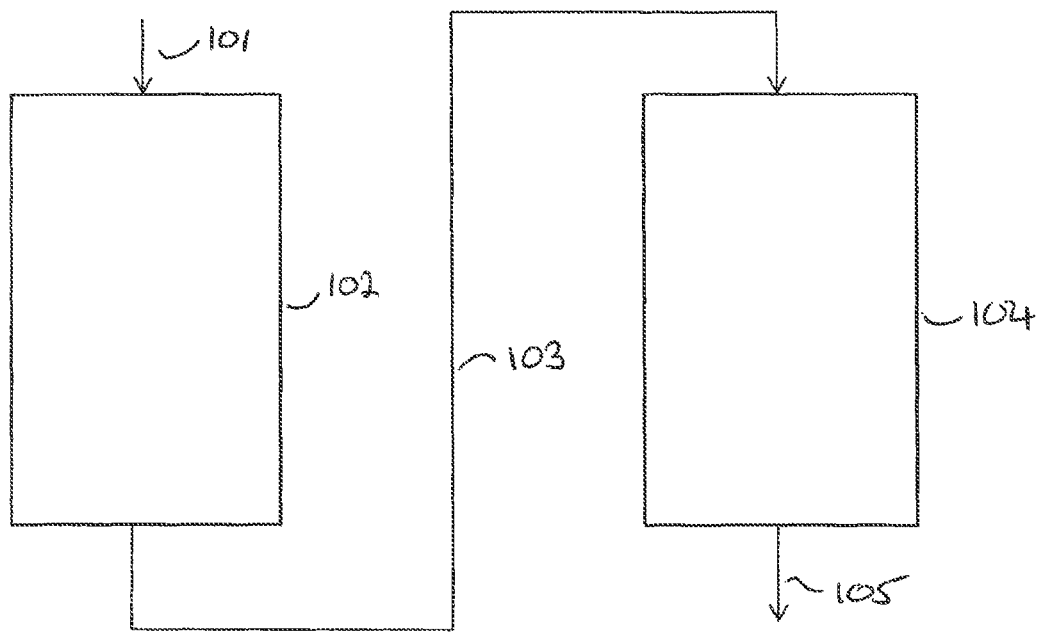
FIG. 1 is a schematic representation of the process of the present invention where the first and second reaction zones are located in separate vessels.

One arrangement of the present invention is described in FIG. 1. A feed of methanol, nitrogen and oxygen is fed in line 101 to the first reaction zone 102. The first reaction zone is a fixed bed reactor 103. Any suitable configuration of fixed bed reactor may be used. Coolant is supplied to the shell of the reactor. The reactor tubes are packed with a first catalyst, generally an iron/molybdenum oxide catalyst, which will generally be of from about 1 mm to about 6 mm. As the reactants travel through the catalyst bed, reaction of some of the methanol occurs to the desired formaldehyde. The length of the reactor tubes is generally selected so that about 50% of the methanol is reacted in the first reactor zone. An intermediate stream comprising the unreacted methanol, nitrogen and oxygen and product formaldehyde is removed as intermediate stream 103 and passed to second reaction zone 104.

The second reaction zone 104 is configured to allow a small catalyst particle equivalent diameter catalyst to be used. In a preferred arrangement, the reactor comprises a plurality of tubes packed with catalyst carriers containing a second catalyst of a second catalyst catalyst particle equivalent diameter which is smaller than that used in the first reaction zone 102. In one arrangement, the catalyst is an iron/molybdenum oxide catalyst of about 0.5 mm diameter. As the reactants travel through the catalyst beds in the carrier, reaction of remaining methanol occurs to the desired formaldehyde.

The product stream is recovered in line 105.

Figure 2:
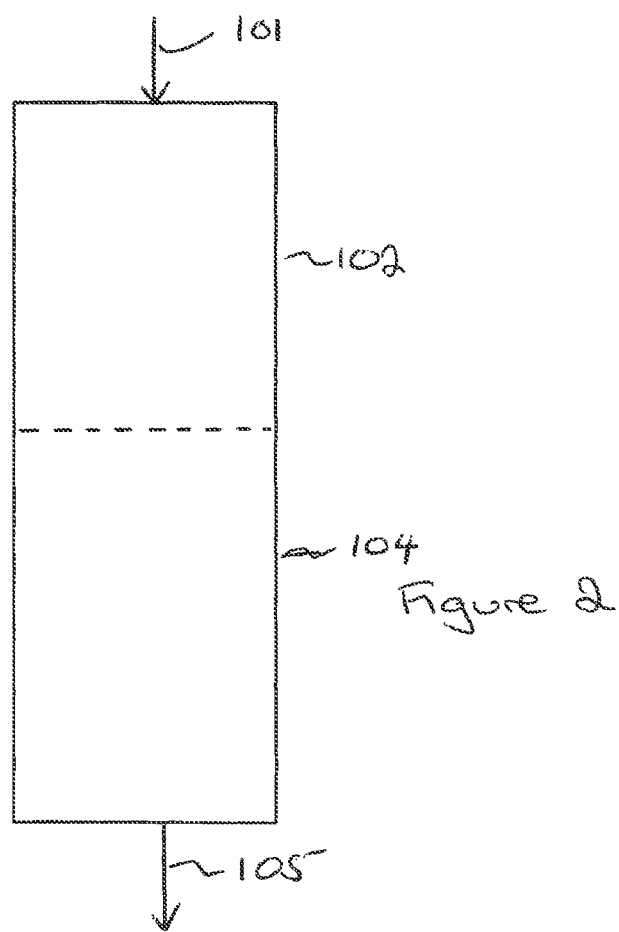
FIG. 2 is a schematic representation of the process of the present invention where the first and second reaction zones are located in the same vessels.

An alternative arrangement is illustrated in FIG. 2 where the first reaction zone 102 and the second reaction zone 104 are located in the same vessel.

Figure 3:
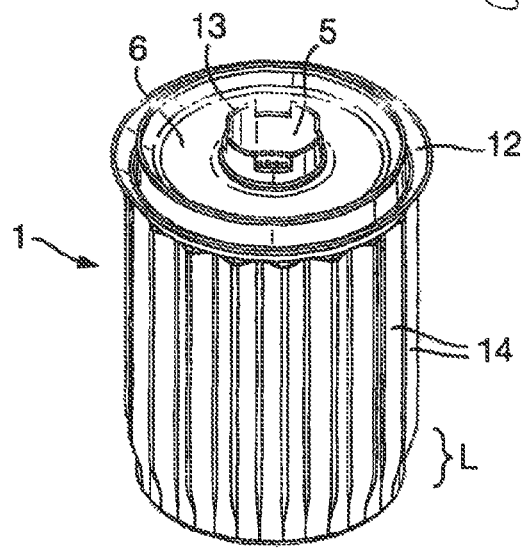
FIG. 3 is a perspective view from above of one example of a catalyst carrier which may be used in the second reaction zone.
Figure 4:
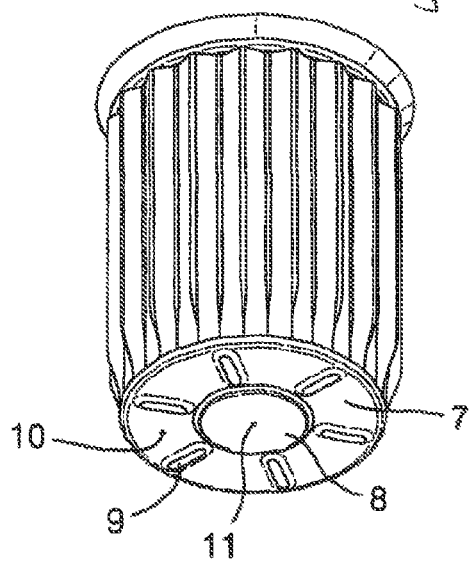
FIG. 4 is a perspective view of the catalyst carrier of FIG. 3 from below.
Figure 5:
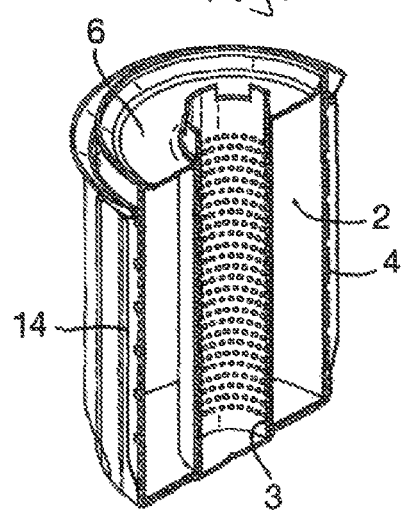
FIG. 5 is a partial cross section viewed from the side.

Any suitable catalyst carrier may be used in the second reaction zone 104. In one arrangement the catalyst carrier is of the kind illustrated in FIGS. 3 to 5. The carrier comprises an annular container 2 which has perforated walls 3, 4. The inner perforated wall 3 defines a tube 5. A top surface 6 is closes the annular container at the top. It is located at a point towards the top of the walls 3, 4 of the annular container 2 such that a lip 6 is formed. A bottom surface 7 closes the bottom of the annular container 2 and a surface 8 closes the bottom of tube 5. The surface 8 is located in a lower plane that that of the bottom surface 7. Spacer means in the form of a plurality of depressions 9 are located present on the bottom surface 7 of the annular container 2. Drain holes 10, 11 are located on the bottom surface 7 and the surface 8.

A seal 12 extends from the upper surface 6 and an upstanding collar 13 is provided coaxial with the tube 5.

A corrugated upstanding skirt 14 surrounds the container 2. The corrugations are flattened in the region L towards the base of the carrier 1.

Figure 6:
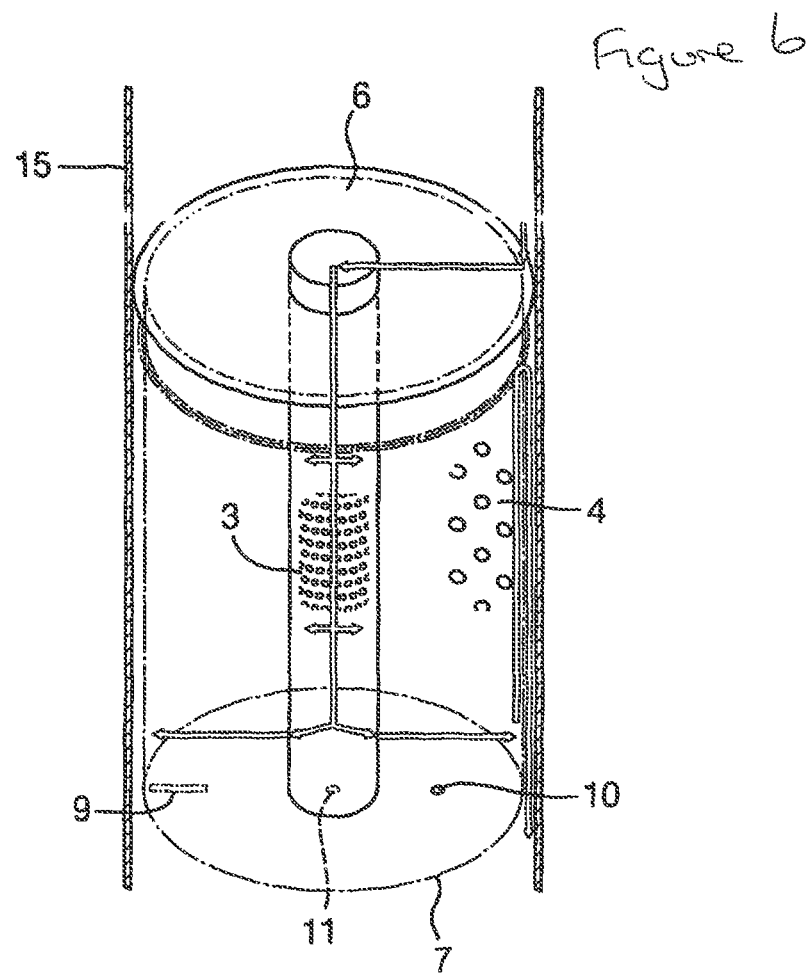
FIG. 6 is a simplified diagram of the catalyst carrier of FIG. 3.
Figure 7:
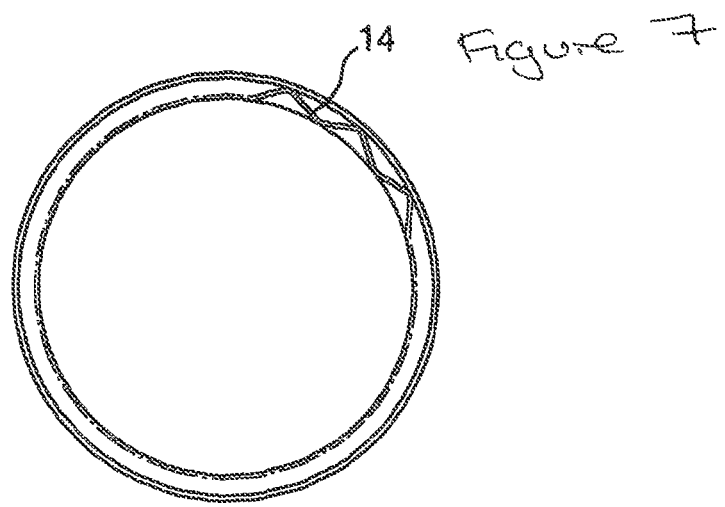
FIG. 7 is a schematic illustration of a carrier of the present invention from below when located within a tube.

A catalyst carrier 1 of the present invention located in a reactor tube 15. The flow of gas is illustrated schematically in FIG. 6 by the arrows.

Figure 8:
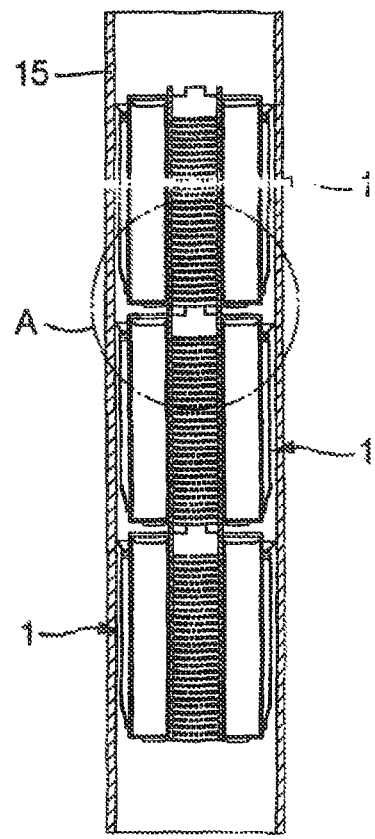
FIG. 8 is a schematic cross section of three catalyst carriers located within a tube.
Figure 9:
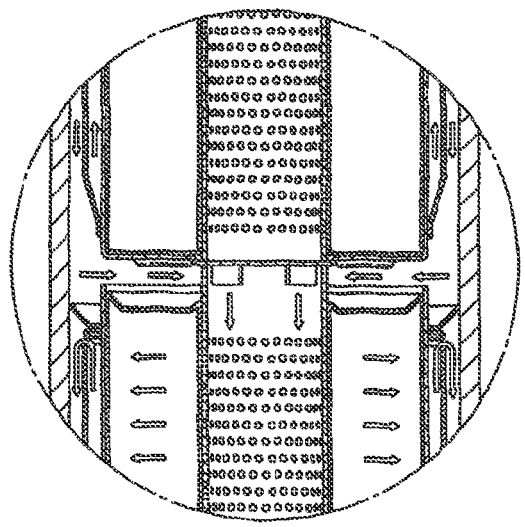
FIG. 9 is an enlarged cross-section of Section A of FIG. 8.

When a plurality of catalyst carriers of the present invention are located within a reactor tube 15 they interlock as illustrated in FIGS. 8 and 9. The effect on the flow path is illustrated in the enlarged section shown in FIG. 9.

The present invention will now be further described by reference to the accompanying examples.

EXAMPLE 1 AND COMPARATIVE EXAMPLE 1

Two reactions for the production of formaldehyde from methanol in a reactor in accordance with the present invention (Example 1) and in a conventional reactor (Comparative Example 1) were carried out. In both reactions, the reactor was operated at 270° C. inlet temperature and at a pressure of 1.71 bar(a). The same inlet composition of 10 mol % methanol was used in each. The results are set out in Table 1.

TABLE 1

|  | CO Concentration (mol %) | Yield | Methanol Conversion |
|---|---|---|---|
| Example 1 | 0.18 | 95.3% | 99.1% |
| Comparative Example 1 | 0.36 | 92.0% | 98.1% |

The "CO concentration" is the CO content in the exhaust gas. The "conversion" is the % of methanol in the reactor feed that has been reacted to formaldehyde, carbon oxides or any other reaction product. "Yield" is the mols of formaldehyde formed divided by the mols of methanol in the reactor feed expressed as a %.

The invention claimed is:

1. A process for carrying out a chemical reaction comprising:
   supplying gaseous reactants to a first reaction zone comprising a first catalyst having a first catalyst particle equivalent diameter;
   operating said first reaction zone such that when the reactants are contacted with the first catalyst a portion of the reactants are converted to a desired product;
   removing an intermediate stream comprising unreacted reactants and the desired product and passing the intermediate stream to a second reaction zone comprising a tubular reactor which comprises tubes, wherein said tubes comprise a plurality of catalyst carriers containing a second catalyst having a second catalyst particle equivalent diameter which is smaller than the first catalyst particle equivalent diameter of the first catalyst;
   operating said second reaction zone such that when the unreacted reactants in the intermediate stream from the first reaction zone are contacted with the second catalyst, at least some of the unreacted reactants are converted to the desired product; and
   recovering a product stream, wherein each catalyst carrier comprises:
   an annular container for holding the second catalyst in use, said container having a perforated inner wall defining a tube, a perforated outer wall, a top surface closing the annular container and a bottom surface closing the annular container;
   a surface closing the bottom of said tube formed by the inner wall of the annular container;
   a skirt extending upwardly from the perforated outer wall of the annular container from a position at or near the bottom surface of said container to a position below the location of a seal;
   and a seal located at or near the top surface and extending from the container by a distance which extends beyond an outer surface of the skirt.

2. The process according to claim 1 wherein interstage cooling is provided between the first and second reaction zones.

3. The process according to claim 1 wherein the first reaction zone comprises a tubular fixed bed reactor.

4. The process according to claim 3 wherein the first and second zones are contiguous and each tube is packed with conventional catalyst in the first zone and with catalyst loaded into catalyst carriers in the second zone.

5. The process according to claim 1 wherein the first catalyst particle equivalent diameter is from about 1 mm to about 6 mm.

6. The process according to claim 1 wherein the second catalyst particle equivalent diameter is from about 0.1 mm to about 3 mm.

7. The process according to claim 1 wherein a portion of the product stream is recycled to at least one of the first and second reaction zones.

8. The process according to claim 1 wherein at least one reactant is one of a) added to the second reaction zone, and b) added to the intermediate stream before it is added to the second reaction zone.

9. The process according to claim 1 wherein the process is for the production of formaldehyde from methanol or methylal.

10. The process according to claim 9 wherein the first catalyst and the second catalyst is a silver catalyst.

11. The process according to claim 9 wherein the first catalyst and the second catalyst is an iron/molybdenum oxide based catalyst.

12. The process according to claim 9 wherein the first reaction zone is sized such that it terminates at a point when about 50% of the methanol or methylal will have been converted.

13. The process according to claim 9 wherein the reactor pressure is from about 1.1 bar(a) to about 10 bar(a).

14. The process according to claim 9 wherein the reactor temperature is from about 250° C. to about 450° C.

15. Apparatus for carrying out a chemical reaction comprising:
   means for supplying gaseous reactants to a first reaction zone comprising a first catalyst having a first catalyst particle equivalent diameter;
   means for removing an intermediate stream comprising unreacted reactants and a desired product and passing the intermediate stream to a second reaction zone comprising a tubular reactor comprising tubes, wherein said tubes comprise a plurality of catalyst carriers containing a second catalyst having a second catalyst particle equivalent diameter which is smaller than the first catalyst particle equivalent diameter of the first catalyst; and
   means for recovering a product stream,
   wherein each catalyst carrier comprises:
   an annular container for holding the second catalyst in use, said container having a perforated inner wall defining a tube, a perforated outer wall, a top surface closing the annular container and a bottom surface closing the annular container;

a surface closing the bottom of said tube formed by the inner wall of the annular container; a skirt extending upwardly from the perforated outer wall of the annular container from a position at or near the bottom surface of said container to a position below the location of a seal;

and a seal located at or near the top surface and extending from the container by a distance which extends beyond an outer surface of the skirt.

16. The apparatus according to claim 15 wherein interstage cooling is provided between the first and second reaction zones.

17. The apparatus according to claim 15 wherein the first reaction zone comprises a tubular fixed bed reactor.

18. The apparatus according to claim 15 further comprising means to recycle a portion of the product stream to at least one of the first and second reaction zones.

19. The apparatus according to claim 15 further comprising one of a) means for adding at least one reactant to the intermediate stream before it is added to the second reaction zone, and b) means for adding at least one reactant to the second reaction zone.

20. The apparatus according to claim 15 wherein the first reaction zone is sized such that it terminates at a point when about 50% of the gaseous reactants will have been converted.

* * * * *